United States Patent [19]

Cacheris et al.

[11] Patent Number: 5,087,440

[45] Date of Patent: Feb. 11, 1992

[54] HETEROCYCLIC DERIVATIVES OF DTPA USED FOR MAGNETIC RESONANCE IMAGING

[75] Inventors: William P. Cacheris, San Jose; Stephen C. Quay, Sunnyvale, both of Calif.

[73] Assignee: Salutar, Inc., Sunnyvale, Calif.

[21] Appl. No.: 468,948

[22] Filed: Jan. 23, 1990

Related U.S. Application Data

[63] Continuation-in-part of Ser. No. 386,807, Jul. 31, 1989, abandoned, which is a continuation-in-part of Ser. No. 314,729, Feb. 23, 1989, abandoned, which is a continuation-in-part of Ser. No. 249,746, Sep. 27, 1988, abandoned.

[51] Int. Cl.$^5$ .................... G01N 31/00; G01N 24/00; A61K 31/555
[52] U.S. Cl. .................... 424/9; 436/173; 514/184; 514/836
[58] Field of Search .................... 424/9; 514/184, 836; 128/654, 653 CA; 436/173

[56] References Cited

U.S. PATENT DOCUMENTS

| | | | |
|---|---|---|---|
| 3,480,715 | 11/1969 | Catsch | 424/289 |
| 3,663,688 | 5/1972 | Grotenhuis | 424/1.1 |
| 4,478,816 | 10/1984 | Ledley et al. | 424/4 |
| 4,714,607 | 12/1987 | Klaveness | 424/9 |
| 4,826,673 | 5/1989 | Dean et al. | 424/9 |

FOREIGN PATENT DOCUMENTS

| | | |
|---|---|---|
| 8188987 | 6/1988 | Australia . |
| 0160552 | 11/1985 | European Pat. Off. . |
| 0210043 | 1/1987 | European Pat. Off. . |
| 0232751 | 8/1987 | European Pat. Off. . |
| 0250358 | 12/1987 | European Pat. Off. . |
| 0258616 | 3/1988 | European Pat. Off. . |
| 029276 | 11/1988 | European Pat. Off. . |
| 0290047 | 11/1988 | European Pat. Off. . |
| 3633243 | 3/1988 | Fed. Rep. of Germany . |
| 8602352 | 4/1986 | PCT Int'l Appl. . |
| 8900052 | 1/1989 | PCT Int'l Appl. . |
| 736432 | 9/1955 | United Kingdom . |
| 2169598 | 7/1986 | United Kingdom . |

OTHER PUBLICATIONS

Weinmann et al., AJR 142:619–624 (1984); "Characteristics of Gadolinium-DTPA Complex: A Potential NMR Contrast Agent".
Nalbandian et al., Ann. NY Acad Sci. (1959) pp. 779–792; "A New Category of Contrast Media: Water-Soluble Radiopaque Polyvalent Chelates".
Sapeika, BMJ, Jul. 16, (1955), pp. 167–169; "Radiographic Use of Lead E.D.T.A. In Man".
Runge et al., Investigative Radiology 19: pp. 408–415; "Paramagnetic NMR Contrast, Agents, Development and Evaluation", (1984).
Ovitt et al., University of Arizona Report No. PB272617 (1977); "Devices and Technology Branch, Division of Heart and Vascular Diseases".
Ovitt et al., University of Arizona Report No. PB8211888 (1979); "Devices and Technology Branch, Division of Heart and Vascular Diseases".
Shapiro et al., Ann. NY Acad, Sci. 78:756–757 (1959); "Heavy-Metal Chelates and Cesium Salts for Contrast Radiography".
Oser et al. Toxicology and Applied Pharmacology 5: 142–162 (1963); "Safety Evaluation Studies of Calcium EDTA".
Rubin et al., Science, 117:659–660 (1953).
Bessman et al., Med. Ann. DC, 21:312–315 (1952).
Belknap, Ind. Med. Surg., 21:305–306 (1952).
Catsch, Chem. Abst., 64:5413h (1966).
Lazlo, USAEC, Orins-12, 193–221 (1956).
Hart, USAEC, Orins-12, 118–135 (1956).
Lafuma, Proceedings of a Symposium on the Diagnostic Treatment of Deposited Radionuclides, (1967), 294–297.
Fried et al., Proc. Soc. Exptl. Biol. Med., 100:570–573 (1959).
Jones et al., J. Chem. Educ., 53:342–347 (1976).
Runge et al., Radiology, 153:171–176 (1984).
Kossakowski, Bull. Vet. Inst. Pulawy, 21:104–108 (1977).
Rosoff et al., Proceedings of the Fifteenth Annual Hanford Life Sciences Symposium, (1977), pp. 547–459.

*Primary Examiner*—Richard L. Raymond
*Assistant Examiner*—Gary E. Hollinden
*Attorney, Agent, or Firm*—Cushman, Darby & Cushman

[57] ABSTRACT

Gadolinium and calcium chelates of DTPA (diethylenetriaminepentaacetic acid) bisamides, such as a composition comprising a gadolinium chelate of a 6-carboxymethyl-3,9-bis (hydroxyalkyl-carbamoylmethyl)-3,6,9-triazaundecanedioic acid and a calcium chelate of a 6-carboxymethyl-3,9-bis(hydroxyalkyl-carbamoylmethyl)-3,6,9- triazaundecanedioic acid, are disclosed for use as magnetic resonance imaging contrast media.

26 Claims, No Drawings

HETEROCYCLIC DERIVATIVES OF DTPA USED FOR MAGNETIC RESONANCE IMAGING

RELATIONSHIP TO COPENDING APPLICATIONS

This application is a continuation-in-part of copending U.S. Pat. application Ser. No. 386807 filed on July 31, 1989 now abandoned, itself a continuation-in-part of copending U.S. Pat. application Ser. No. 314729 filed on Feb. 23, 1989 now abandoned which is itself a continuation-in-part of copending U.S. Pat. application Serial No. 249746 filed on Sept. 27, 1988, now abandoned.

FIELD OF THE INVENTION

This invention relates to magnetic resonance imaging (MRI) contrast agents and their use in magnetic resonance imaging. In particular, this invention relates to compositions comprising gadolinium and calcium chelates of diethylenetriaminepentaacetic acid bisamides (DTPA - bisamides) and the use of such compositions as MRI contrast media.

BACKGROUND TO THE INVENTION

In MRI, the contrast in the images generated may be enhanced by introducing into the zone being imaged an agent, generally referred to as a contrast agent, which affects the nuclear spin reequilibration characteristics of the nuclei (generally water protons in body tissues or fluids) which are responsible for the magnetic resonance signals from which the MR images are generated.

Thus, for example, in 1978 Lauterbur proposed the use of paramagnetic species, such as Mn(II), as MRI contrast agents (see Lauterbur et al., pages 752-759 in "Electrons to Tissues - Frontiers of Biological Energetics", Volume 1, edited by Dutton et al., Academic Press, N.Y., 1978) and more recently Schering AG, in U.S. Pat. No. 4647447, proposed the use of the dimeglumine salt of the gadolinium (III) chelate of diethylenetriaminepentaacetic acid (Gd DTPA).

Gadolinium (III) compounds are particularly attractive as MRI contrast agents due to the large magnetic dipole of $Gd^{3+}$.

However, the usefulness of even high stability constant chelates such as Gd DTPA could be limited since the dosage required for imaging certain organs may possibly be too toxic for safe and effective use and, as Schering AG have themselves disclosed, there is a problem of gadolinium retention following iv administration of Gd DTPA (see AU-81889/87).

Gd DTPA-bis(hydroxylated alkylamides) have proven to be substantially less toxic than Gd DTPA and thus to be utilizable in higher dosages and for imaging of a wider variety of organs than Gd DTPA. Gd DTPA-bis(hydoxylated alkylamides) are disclosed in U.S. Pat. No. 4826673 (Dean) and EP-A-130934 (Schering AG).

The present invention provides compositions containing DTPA-bis(hydroxylated alkylamide) (DTPA-BHA) chelates of both gadolinium and calcium, compositions which exhibit lower toxicities than Gd DTPA or Gd and DTPA-BHA, and which can therefore be safely administered in even higher doses than Gd DTPA or Gd DTPA-BHA.

DESCRIPTION OF PRIOR ART

In AU-81889/87, which corresponds to EP-A-270483, Schering AG disclosed that they have found that in vivo release of the heavy metal (i.e. gadolinium) from heavy metal complexes is reduced by formulating the heavy metal complex together with one or more weaker metal complexes and/or one or more free complexing agents. As suitable weaker metal complexes Schering AG suggest the use of complexes having as the central atom a calcium, magnesium, zinc or iron atom, but give no indication as to whether any of these might be preferred above the others. The experimental results contained in AU-81889/87 relate to the reduction in gadolinium retention in the rat following iv administration of Gd DTPA that is achieved by inclusion with the Gd DTPA of free chelating agent (i.e. DTPA) or of CaNa$_3$DTPA.

Schering AG on page 11 of AU-81889/87, state that the addition of free complexing agents or weak complexes has an "extraordinarily strong" effect with reference to the stability of the bonding of the heavy metal and thus its detoxification and elimination. However, this statement is qualified by a reference to the effect that a higher toxicity may need to be accepted as the price for this advantage.

The use of excess chelating agent in paramagnetic metal chelate-containing MRI contrast agents is also disclosed in Examples 33 and 34 of U.S. Pat. No. 4714607 (Klaveness) and in U.S. Pat. No. 4826673 (Dean).

SUMMARY OF THE INVENTION

The present invention is based on the surprising discovery that the inclusion of the calcium chelate of DTPA-BHA in Gd DTPA-BHA-containing MRI contrast media results in an unpredictably large reduction in the acute toxicity of the composition.

Thus in one aspect the invention provides a magnetic resonance imaging contrast medium comprising a gadolinium chelate of a 6-carboxymethyl-3,9-bis(hydroxyalkylcarbamoylmethyl)-3,6,9-triazaundecanedioic acid (hereinafter referred to as a DTPA-BHA) and a toxicity reducing amount of a calcium chelate of a 6-carboxymethyl-3,9-bis(hydroxy-alkylcarbamoylmethyl)-3,6,9-triazaundecanedioic acid.

Preferably, the chelates in the contrast media of the invention are chelates with compounds of formula I:

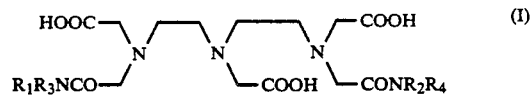

(I)

(wherein $R_1$ and $R_2$ are independently $C_{1-6}$ hydroxyalkyl and $R_3$ and $R_4$ are independently hydrogen or $C_{1-6}$ alkyl or either or both of $NR_1R_3$ and $NR_2R_4$ are independently a group of formula

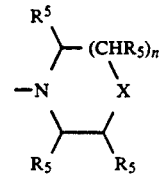

wherein $R_5$ represents hydrogen, hydroxy or $C_{1-6}$ optionally hydroxy- or alkoxy-substituted alkyl, n is 0, 1 or 2 and X is $CHR_5$, $NR_5$, oxygen or sulphur, $CHR_5$ being preferred where n is zero).

Particularly preferably $NR_1R_3$ and $NR_2R_4$ both represent groups of formula

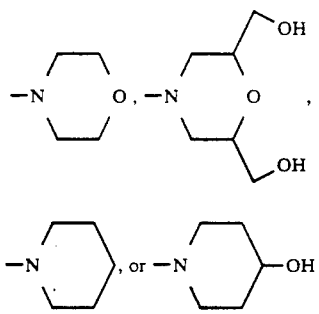

Preferred compounds of formula I include those wherein $R_1$ and $R_2$ both represent dihydroxypropyl and wherein $R_3$ and $R_4$ both represent hydrogen or methyl, or wherein $NR_1R_3$ and $NR_2R_4$ both represent a group of formula

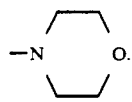

Especially preferred chelating agents of formula I include 6-carboxymethyl-3,9-bis(N-methyl-N-2,3-dihydroxypropyl-carbamoylmethyl)-3,6, 9-triazaundecane dicarboxylic acid (DTPA-BMPA), 6-carboxymethyl-3,9-bis(2, 3-dihydroxypropylcarbamoylmethyl)-3,6,9-triazaundecanedioic acid (DTPA-APD) and 6-carboxymethyl-3,9-bismorpholide-3,6,9-triazaundecanoic acid (DTPA-BMO).

Particularly preferably, the chelating moieties in the gadolinium and calcium chelates in the contrast media of the invention are the same.

In a further aspect the invention also provides a method of magnetic resonance imaging of a human or nonhuman animal, preferably mammalian, subject, the improvement comprising administering to said subject a contrast effective amount of a contrast medium according to the invention.

In the contrast media of the invention, the molar ratio of the calcium chelate to the gadolinium chelate is conveniently within the range of from 1:200 to 1:5, preferably 1:100 to 1:10, especially 1:30 to 1:15 and particularly about 1:20.

DETAILED DESCRIPTION OF THE INVENTION

Without being limited to a particular theory of interaction which might underly the surprising effectiveness of the contrast media of the invention the principal toxicity of non-ionic gadolinium chelates, e.g. Gd DTPA-bismethylamide, is believed to derive from the displacement of the gadolinium ion from the chelate by endogenous metal ions (especially Zn(II)) normally present in the body. When administering the contrast media of this invention, the Zn(II) available for displacement is believed to preferentially displace the calcium from the DTPA-BHA, liberating non-toxic calcium into the blood, and leaving the gadolinium ion secure in a stable chelate. The DTPA-amide chelates have been found to be uniquely suitable for improving toxicity, apparently because they act in a unique manner in this interaction. Administration of gadolinium and calcium chelates of non-amide chelates has not been found to provide a significant improvement in toxicity. With the reduced toxicity provided by the contrast media of this invention, image contrast with MRI procedures can be increased with greater safety, and higher dosages of the contrast agent can be safely administered, providing contrast for imaging a wider range of organs.

DTPA-BHAs and methods for their preparation are described in U.S. Pat. No. 4826673 and EP-A-130934. The contents of all of the above documents are hereby incorporated by reference in their entireties.

The calcium chelates may be prepared by mixing a molar equivalent amount of calcium hydroxide or a soluble calcium salt with the DTPA-BHA in aqueous solution in a conventional manner. The calcium chelate in aqueous solution is preferably a fully neutralized salt. The salt ion can be of any pharmaceutically acceptable, non-toxic ion. Suitable salts include monovalent cations such as ions of lithium, potassium, and sodium. Divalent cations such as calcium and magnesium can also be used. Suitable cations of organic bases include, for example, ethanolamine, diethanolamine, morpholine, glucamine, N,N-dimethylglucamine, N-methylglucamine. Salts of basic amino acids such as lysine, arginine or ornithine are suitable as cations of amino acids, as generally are those of other basic naturally occurring acids.

The contrast medium of the invention should contain a sufficient amount of the calcium chelate to reduce the toxicity of the composition relative to that of the gadolinium chelate, any amount present generally providing some improvement. The amount of calcium chelate present, however, must be below toxic limits. Preferred compositions have a molar ratio of calcium chelate to gadolinium chelate within the range of from 1:200 to 1:10 and preferably from 1:100 to 1:20. The dosage amount of calcium chelate can conveniently be at physiologically tolerable level within the range from 0.001 to 1 mmol/kg and preferably from 0.004 to 0.08 mmol/kg of patient body weight.

Moreover, it is believed that the presence of the calcium chelate in the contrast media of the invention improves the biotolerability of the gadolinium chelate by hindering displacement of gadolinium from the chelate by zinc ions. It may therefore be desirable to match the concentration or dosage of calcium chelate to the plasma zinc concentration of the subject to which or to whom the contrast medium is to be administered.

The contrast media according to this invention can conveniently contain from 0.001 to 5.0 moles per liter and preferably from 0.1 to 1.2 moles per liter of the gadolinium chelate.

The contrast media of this invention are administered to patients for imaging in amounts which are sufficient to yield the desired contrast. Generally, dosages of from 0.001 to 5.0 mmoles of gadolinium chelate per kilogram of patient body weight are effective to achieve adequate contrast enhancement. The preferred dosages for most MRI applications are from 0.02 to 1.2 mmoles of gadolinium chelate per kilogram of patient body weight.

The contrast media of the present invention may be formulated with conventional pharmaceutical or veterinary formulation aids, for example stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the contrast media of the present invention may be in conventional pharmaceutical adminstration forms such as tablets, capsules, powders, solutions, suspensions, dispersions, syrups, suppositories etc.; however, solutions, suspensions and dispersions in physiologically acceptable carrier media, for example water for injections, will generally be preferred.

The contrast media according to the invention may therefore be formulated for administration using physiologically acceptable carriers or excipients in a manner fully within the skill of the art. For example, the chelate components, optionally with the addition of pharmaceutically acceptable excipients, may be suspended or dissolved in an aqueous medium, with the resulting solution or suspension then being sterilized. As mentioned above, suitable additives include, for example, physiologically biocompatible buffers (as, for example, tromethamine hydrochloride), slight additions of other chelating agents (as for example, diethylenetriaminepentaacetic acid) or, optionally, calcium or sodium salts (for example, calcium chloride, calcium ascorbate, calcium gluconate or calcium lactate).

If the contrast media are to be formulated in suspension form, e.g. in water or physiological saline for oral administration, a small amount of soluble chelate salt may be mixed with one or more of the inactive ingredients traditionally present in oral solutions and/or surfactants and/or aromatics for flavouring.

The most preferred mode for administering paramagnetic metal chelates as contrast agents for MRI is parenteral, e.g. intravenous, administration. Parenterally administrable forms, e.g. intravenous solutions, should be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON'S PHARMACEUTICAL SCIENCES, 15th Ed., Easton: Mack Publishing Co, pp 1405-1412 and 1461-1487 (1975) and THE NATIONAL FORMULARY XIV, 14th Ed. Washington: American Pharmaceutical Association (1975), the contents of which are hereby incorporated by reference. The solutions can contain preservatives, antimicrobial agents, buffers and antioxidants conventionally used in parenteral solutions, excipients and other additives which are compatible with the chelates and which will not interfere with the manufacture, storage or use of the products.

The contrast media of the invention may also, of course, be in concentrated or dried form for dilution prior to administration.

Methods for applying contrast media to improve MR images, MRI equipment and MRI operating procedures are described by Valk, J. et al., BASIC PRINCIPLES OF NUCLEAR MAGNETIC RESONANCE IMAGING, New York: Elsevier, pp 109-114 (1985). The contents of the Valk et al. publication are hereby incorporated by reference in their entirety.

With the contrast media of this invention, effective imaging contrast can be obtained with a wider variety of organs such as kidney, urethra, bladder, brain, spine, heart, liver, spleen, adrenal glands, ovaries, skeletal muscle and the like.

This invention is further illustrated by the following specific but non-limiting examples. Temperatures are given in degrees Celsius and concentrations as weight percents unless otherwise specified.

EXAMPLE 1

DTPA-bis-(2,3-diydroxypropylamide) Dihydrate

A mixture of 54.8 g (600 mmol) of 3-amino-1,2-propanediol, 84 mL (600 mmol) triethylamine, and 200 mL dimethyl sulfoxide (DMSO) were combined with stirring at room temperature. DTPA anhydride (71.5 g; 200 mmol) was added in portions over 10 min. After stirring for 2 hrs at room temperature, the amber reaction mixture was concentrated under reduced pressure The crude reaction product was adjusted to pH 3.5 with 6 N HCl and then chromatographed on a column of AG1-X4 anion exchange resin (acetate form). The product was eluted with 1 N acetic acid to provide 103 g (89%) of DTPA bis-(2,3-dihydroxypropylamide) dihydrate (DTPA-APD dihydrate) as an oil. Lyophilization provided a colorless solid which was determined to possess two waters of hydration.

EXAMPLE 2

Gd DTPA-APD

Gadolinium oxide (18.128 g; 50 mmol) and 54 g (94 mmol) DTPA-APD dihydrate were combined in 60 mL water and heated under reflux. Additional DTPA-APD dihydrate was added in small portions over 6 hours at reflux until a xylenol orange test for excess gadolinium ion was negative. A total of 57.75 g (100 mmol) ligand was necessary. After cooling, the reaction mixture was diluted to 150 mL with water and filtered (0.2 micron membrane filter). This 667 mM Gd DTPA-APD solution was used for the formulations described in Examples 4 and 5.

EXAMPLE 3

NaCa DTPA-APD

DTPA-APD dihydrate (1.44 g; 2.5 mmol) and calcium hydroxide (186 mg; 2.5 mmol) were combined in 3 mL water and adjusted to pH 6.6 by the addition of ca. 1.5 mL 1 N NaOH solution. This was used directly for a formulation described in Example 5.

EXAMPLE 4

Preparation of 500 mM Gd DTPA-APD

A 67.5 mL (45 mmol) portion of the 667 mM Gd DTPA-APD stock solution described in Example 2 was adjusted to pH 6.0 with 1 N NaOH solution. After dilution to 90 mL, the resulting 500 mM Gd DTPA-APD solution was sterile-filtered into serum vials and autoclaved 30 minutes at 121° C.

EXAMPLE 5

Formulation of 500 mM Gd DTPA-APD and 25 mM Ca Na DTPA-APD Solution

A 75 mL (50 mmol) portion of the 667 mM Gd DTPA-APD stock solution described in Example 2 was combined with the Na Ca DTPA-APD preparation (2.5 mmol) of Example 3. The resulting solution was adjusted to pH 5.9 with 1N NaOH and diluted to 100 mL. The solution was sterile-filtered into serum vials and autoclaved 30 minutes at 121° C.

EXAMPLE 6

DTPA-bis(N-methyl-2,3-diydroxypropylamide)

N-methylaminopropanediol (50.0 g, 139.9 mmol) was dissolved in DMSO (250 mL), and DTPA-bisanhydride was added under a nitrogen atmosphere. After stirring overnight (10 hours), the product was precipitated with a 1:1 mixture of ether and chloroform. The crystals were dissolved in water (150 mL) and precipitated once more with ethanol (1400 mL). After 1 hour, the product was separated from the solvent. Stirring with ethanol (600 mL) produced a white powder which was dried in vacuum. The yield of DTPA-bis-(N-methyl-2,3-dihydroxypropylamide) (DTPA-BMPA) was 45.0 g (56%). Mp. 75°–80° C. FAB-MS: 568(M+1).

EXAMPLE 7

Gd DTPA-BMPA

DTPA-BMPA (39.0 g, 68.7 mmol) was dissolved in water (50 mL). The water was distilled off to remove ethanol; the oil was dissolved in water (250 mL); and $Gd_2O_3$ (11.2 g, 31.0 mmol) was added. The mixture was stirred for 16 hours at 100° C. and filtered, and the solvent was removed. The product was dissolved in methanol (110 mL) and precipitated with acetone (250 mL). The product was dissolved in water and dried. This was repeated two times to remove traces of acetone. Yield 40.4 g (81%). Mp. 280° C. FAB-MS: 723(M+1).

Anal Calcd. for $C_{22}H_{38}GdN_5O_{12}$: C,35.60; H,5.31; N,9.70.

Found: C,36.12; H,5.25; N,10.39.

EXAMPLE 8

NaCa DTPA-BMPA

DTPA-BMPA (5.0 g, 8.8 mmol) was dissolved in water (50 mL), and $Ca(OH)_2$ (0.65 g, 8.8 mmol) was added. The mixture was stirred at room temperature for about 1.5 hours. The solution was neutralized with 2 M NaOH and then filtered. The filtrate was evaporated to dryness, and the NaCa DTPA-BMPA compound was isolated as a white powder. Yield 5.2 g (84%). Mp. 230°–233° C. FAB-MS: 628 (M+1)

Anal. Calcd. for $C_{22}H_{38}CaN_5NaO_{12}$: C,42.10;H,6.10;N,11.16.

Found: C,41.48;H,5.96;N,10.96.

EXAMPLE 9

Gd DTPA-BMPA and NaCa DTPA-BMPA Solution

Gd DTPA-BMPA (3.61 g, 5 mmol) and NaCa DTPA-BMPA (0.157 g, 0.25 mmol) were dissolved in water (7 mL). The pH was adjusted to between 5.5 and 6.5 and water (to 10 mL) was added. The solution was sterile filtered into a 10 mL vial. The solution contained 0.5 mmol of Gd per mL.

EXAMPLE 10

DTPA-bismorpholide (DTPA-BMO)

To a 2-liter round bottom flask containing morpholine (400 mL, 4.60 mol) was added DTPA dianhydride (71.5 g, 200 mmol) followed by 150 mL of water. The reaction was stirred for 24 hours and concentrated. The crude material was evaporated three times from 400 mL water and then stirred with 1 L of dry ethanol at 50° C. for 18 hours. The suspension was filtered and the solids were purified by ion-exchange chromatography on AG1-X8 (hydroxide form) resin eluting with water followed by 0.2 N acetic acid to afford 53.0 g of DTPA-BMO.

Anal. calcd. for $C_{22}G_{37}N_5O_{10}$ 1.25$H_2O$:
C, 47.69; H, 7.19, N, 12.64.

Found: C, 47.48; H, 7.29; N 12.42

EXAMPLE 11

Gd DTPA-BMO

To DTPA-BMO (33.0 g, 60 mmol) in 110 mL water was added $Gd(OAc)_3$ $4H_2O$ (24.4 g, 60 mmol). The reaction was stirred overnight and then lyophilized five times to provide 41.0 g of Gd DTPA-BMO as a light yellow solid.

EXAMPLE 12

Formulation of 500 mM Gd DTPA-BMO with 5% CaNa DTPA-BMO

To DTPA-BMO (1.6 g, 3.0 mmol) in 10 mL of water was added $Ca(OH)_2$ (0.22 g, 3.0 mmol) followed by 3.0 mL of 1N NaOH to adjust the pH to 6.5. This solution was added to Gd DTPA-BMO (41.0 g, 60.0 mmol) dissolved in 90 mL of water. The pH of the combined solutions was adjusted to 6.5 with 1 N NaOH and the volume adjusted to 120 mL with additional water.

EXAMPLE 13

Acute Toxicity

Acute toxicity ($LD_{50}$) values were determined for compositions comprising 500 mM Gd DTPA-APD alone or together with 25 mM of the calcium chelate of DTPA-APD and, for further comparison, for compositions comprising 500 mM Gd DTPA-dimeglumine alone or together with 25 mM of a calcium chelate of DTPA or a DTPA-bisamide (the bismethylamide. The acute toxicities were determined by iv administrations of the compositions to Swiss Webster mice.

| Gd chelate | Added chelate | $LD_{50}$ (iv mice, mmol/kg) |
|---|---|---|
| Gd DTPA* | None | 5.5 |
| Gd DTPA* | Ca DTPA++ | 4.5 |
| Gd DTPA* | Ca DTPA-bismethylamide+ | 4.4 |
| Gd DTPA-APD | None | 13.8 |
| Gd DTPA-APD | Ca DTPA-APD+ | 44.0 |

*as the dimeglumine salt
+as the sodium salt
++as the trisodium salt

The results set forth above clearly show the unpredicted and surprising reduction in MRI contrast medium toxicity achievable using the present invention.

We claim:

1. A magnetic resonance imaging contrast medium comprising a gadolinium chelate of a compound of formula I:

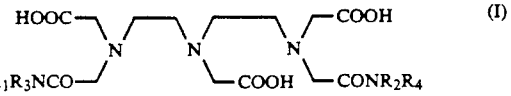

wherein $R_1$ and $R_2$ are independently $C_{1-6}$ hydroxyalkyl and $R_3$ and $R_4$ are independently hydrogen or $C_{1-6}$ alkyl, or $NR_1R_3$ and $NR_2R_4$ are independently a cyclic group of formula:

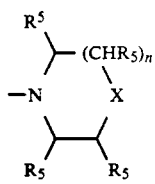

wherein $R_5$ represents hydrogen, hydroxy or $C_{1-6}$ hydroxy- or alkoxy-substituted alkyl, n is 0, 1 or 2 and X is $CHR_5$, $NR_5$, oxygen or sulfur, with the proviso that at least one of $NR_1R_3$ and $NR_2R_4$ is a said cyclic group, and a toxicity reducing amount of a calcium chelate of a compound of formula I.

2. A medium as claimed in claim 1 comprising calcium and gadolinium chelates of compounds of formula I wherein $NR_1R_3$ and $NR_2R_4$ represent morpholinyl groups.

3. A medium as claimed in claim 1 comprising calcium and gadolinium chelates of 6-carboxylmethyl-3,9-bismorpholide-3,6,9-triazaundecanedioic acid.

4. A medium as claimed in claim 1 wherein the molar ratio of calcium to gadolinium is in the range 1:200 to 1:5.

5. A medium as claimed in claim 1 wherein the molar ratio of calcium to gadolinium is in the range 1:200 to 1:10.

6. A medium as claimed in claim 1 wherein the molar ratio of calcium to gadolinium is in the range 1:100 to 1:20.

7. A medium as claimed in claim 1 wherein the molar ratio of calcium to gadolinium is about 1:20.

8. A medium as claimed in claim 1 wherein said gadolinium chelate is present at a concentration of 0.001 to 5.0 moles/liter.

9. A medium as claimed in claim 1 wherein said gadolinium chelate is present at a concentration of 0.1 to 1.2 moles/liter.

10. A medium as claimed in claim 4 wherein said gadolinium chelate is present at a concentration of 0.1 to 1.2 moles/liter.

11. A medium as claimed in claim 5 wherein said gadolinium chelate is present at a concentration of 0.1 to 1.2 moles/liter.

12. A medium as claimed in claim 6 wherein said gadolinium chelate is present at a concentration of 0.1 to 1.2 moles/liter.

13. A medium as claimed in claim 7 wherein said gadolinium chelate is present at a concentration of 0.1 to 1.2 moles/liter.

14. A medium as claimed in claim 1 comprising said chelates in solution in a sterile physiologically tolerable aqueous carrier medium.

15. In a method of magnetic resonance imaging of a human or non-human animal subject, the improvement comprising administering to said subject a contrast effective amount of a contrast medium comprising a gadolinium chelate of a compound of formula I:

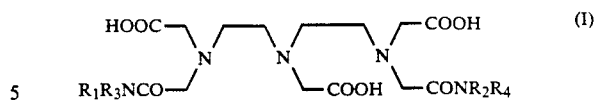

wherein $R_1$ and $R_2$ are independently $C_{1-6}$ hydroxyalkyl and $R_3$ and $R_4$ are independently hydrogen or $C_{1-6}$ alkyl, or $NR_1R_3$ and $NR_2R_4$ are independently a cyclic group of formula:

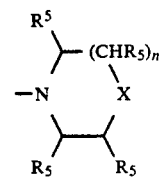

wherein $R_5$ represents hydrogen, hydroxy or $C_{1-6}$ hydroxy- or alkoxy-substituted alkyl, n is 0, 1 or 2 and X is $CHR_5$, $NR_5$, oxygen or sulfur, with the proviso that at least one of $NR_1R_3$ and $NR_2R_4$ is a said cyclic group, and a toxicity reducing amount of a calcium chelate of a compound of formula I.

16. A method as claimed in claim 15 comprising administering a said medium wherein the molar ratio of calcium to gadolinium is in the range 1:200 to 1:5.

17. A method as claimed in claim 15 comprising administering a said medium wherein the molar ratio of calcium to gadolinium is in the range 1:200 to 1:10.

18. A method as claimed in claim 15 comprising administering a said medium wherein the molar ratio of calcium a gadolinium is in the range 1:100 to 1:20.

19. A method as claimed in claim 15 comprising administering a said medium at a dosage of 0.001 to 1 mmoles of said gadolinium chelate/kg bodyweight.

20. A method as claimed in claim 15 comprising administering a said medium at a dosage of 0.02 to 1.2 mmoles of said gadolinium chelate/kg bodyweight.

21. A method as claimed in claim 15 comprising administering a said medium at a dosage of 0.001 to 1 mmoles of said calcium chelate/kg bodyweight.

22. A method as claimed in claim 15 comprising administering a said medium at a dosage of 0.004 to 0.08 moles of said calcium chelate/kg bodyweight.

23. A method as claimed in claim 20 comprising administering a said medium at a dosage of 0.004 to 0.08 mmoles of said calcium chelate/kg bodyweight.

24. A method as claimed in claim 15 wherein said contrast medium is administered intravenously to a human subject.

25. A method as claimed in claim 15 comprising administering a said medium comprising calcium and gadolinium chelates of compounds of formula I wherein $NR_1R_3$ and $NR_2R_4$ represent morpholinyl groups.

26. A method as claimed in claim 15 comprising administering a said medium comprising calcium and gadolinium chelates of 6-carboxymethyl(-3,9-bismorpholide-3,6,9-triazaundecanedioic acid.

* * * * *